(12) United States Patent
Osypka

(10) Patent No.: US 6,684,109 B1
(45) Date of Patent: Jan. 27, 2004

(54) ENDOCARDIAL LEAD

(75) Inventor: Thomas Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 245 days.

(21) Appl. No.: 09/661,118

(22) Filed: Sep. 13, 2000

(51) Int. Cl.[7] ................................. A61N 1/05
(52) U.S. Cl. ..................... 607/122; 607/126
(58) Field of Search ................ 607/119, 125–128, 607/122; 600/374, 375

(56) References Cited

U.S. PATENT DOCUMENTS

| | | | |
|---|---|---|---|
| 3,976,082 A | 8/1976 | Schmitt | |
| 4,567,900 A | 2/1986 | Moore | |
| 4,641,656 A | 2/1987 | Smits | |
| 4,646,755 A | * 3/1987 | Kane | 607/126 |
| 4,662,377 A | 5/1987 | Heilman et al. | |
| 4,662,382 A | * 5/1987 | Sluetz | 607/128 |
| 4,774,952 A | 10/1988 | Smits | |
| 4,796,643 A | * 1/1989 | Nakazawa et al. | 607/128 |
| 4,860,769 A | 8/1989 | Fogarty et al. | |
| 4,917,106 A | 4/1990 | Olivier | |
| 4,945,922 A | 8/1990 | van Krieken | |
| 4,946,457 A | 8/1990 | Elliott | |
| 4,957,118 A | * 9/1990 | Erlebacher | 607/128 |
| 4,974,588 A | 12/1990 | Smits | |
| 5,007,436 A | 4/1991 | Smits | |
| 5,076,285 A | 12/1991 | Hess et al. | |
| 5,133,365 A | 7/1992 | Heil, Jr. et al. | |
| 5,231,996 A | * 8/1993 | Bardy | 607/126 |
| 5,257,634 A | * 11/1993 | Kroll | 607/122 |
| 5,259,395 A | * 11/1993 | Li | 607/131 |
| 5,261,417 A | 11/1993 | Osypka | |
| 5,282,845 A | * 2/1994 | Bush et al. | 607/128 |
| 5,300,107 A | * 4/1994 | Stokes | 607/126 |
| 5,397,341 A | 3/1995 | Hirschberg et al. | |
| 5,411,527 A | 5/1995 | Alt | |
| 5,411,546 A | 5/1995 | Bowald et al. | |
| 5,439,485 A | 8/1995 | Mar et al. | |
| 5,522,876 A | 6/1996 | Rusink | |
| 5,531,779 A | 7/1996 | Dahl et al. | |
| 5,534,022 A | 7/1996 | Hoffmann et al. | |
| 5,542,173 A | * 8/1996 | Mar et al. | 29/825 |
| 5,571,157 A | * 11/1996 | McConnell | 607/116 |
| 5,575,814 A | 11/1996 | Giele et al. | |
| 5,662,698 A | 9/1997 | Altman et al. | |
| 5,772,693 A | * 6/1998 | Brownlee | 607/126 |
| 5,931,862 A | 8/1999 | Carson | |
| 5,957,967 A | 9/1999 | Laske | |
| 6,006,139 A | * 12/1999 | Kruse | 607/125 |
| 6,029,091 A | 2/2000 | de la Rama et al. | |
| 6,050,992 A | 4/2000 | Nichols | |
| 6,185,464 B1 | * 2/2001 | Bonner et al. | 607/119 |
| 6,574,514 B2 | * 6/2003 | Partridge et al. | 607/126 |

FOREIGN PATENT DOCUMENTS

FR    2 724 566    3/1996

OTHER PUBLICATIONS

Oscor Medical Corporation, *The Ends Justify The Means*, May, 1991.
International Search Report dated Jul. 1, 2002.

* cited by examiner

Primary Examiner—Angela D. Sykes
Assistant Examiner—Roderick Bradford
(74) Attorney, Agent, or Firm—Scott D. Wofsy; Edwards & Angell, LLP

(57) ABSTRACT

An endocardial lead is disclosed including an elongated insulative lead body having opposed proximal and distal end portions, and having a lumen extending therethrough, an electrode assembly operatively associated with the distal end portion of the lead body and including a distal electrode having a central portion and structure extending radially therefrom to define the shocking surface of the electrode, a connector assembly operatively associated with the proximal end portion of the lead body, and a conductor assembly extending through the lumen of the lead body to electrically join the electrode assembly and the connector assembly.

18 Claims, 7 Drawing Sheets

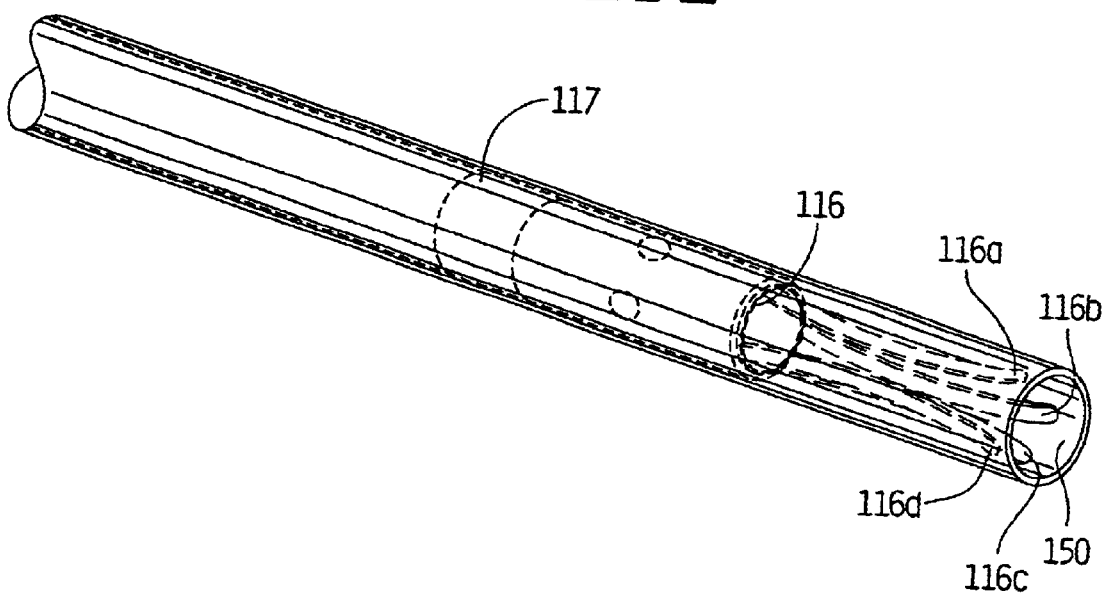
FIG_2
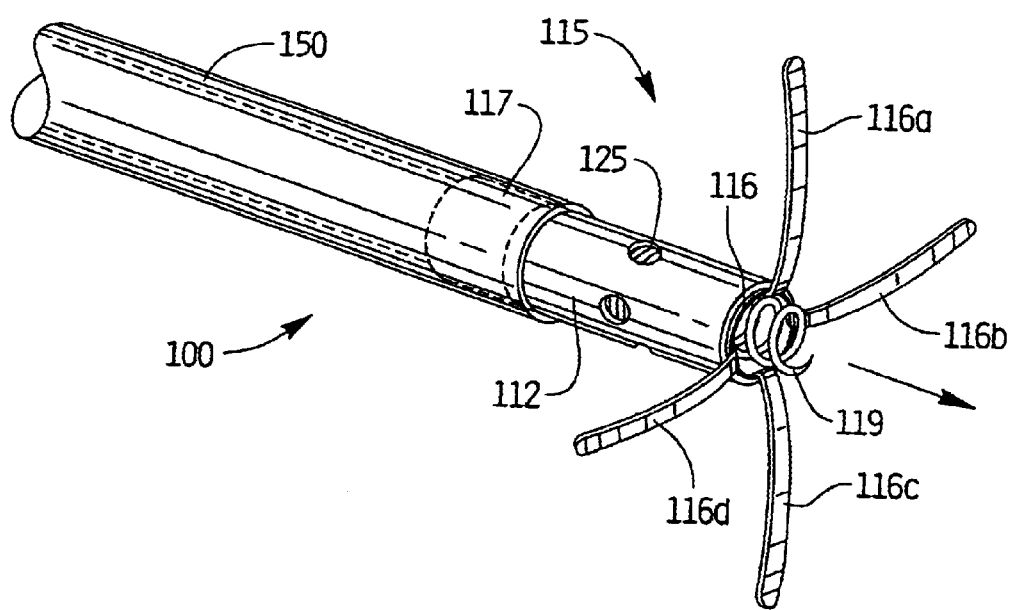
FIG_3

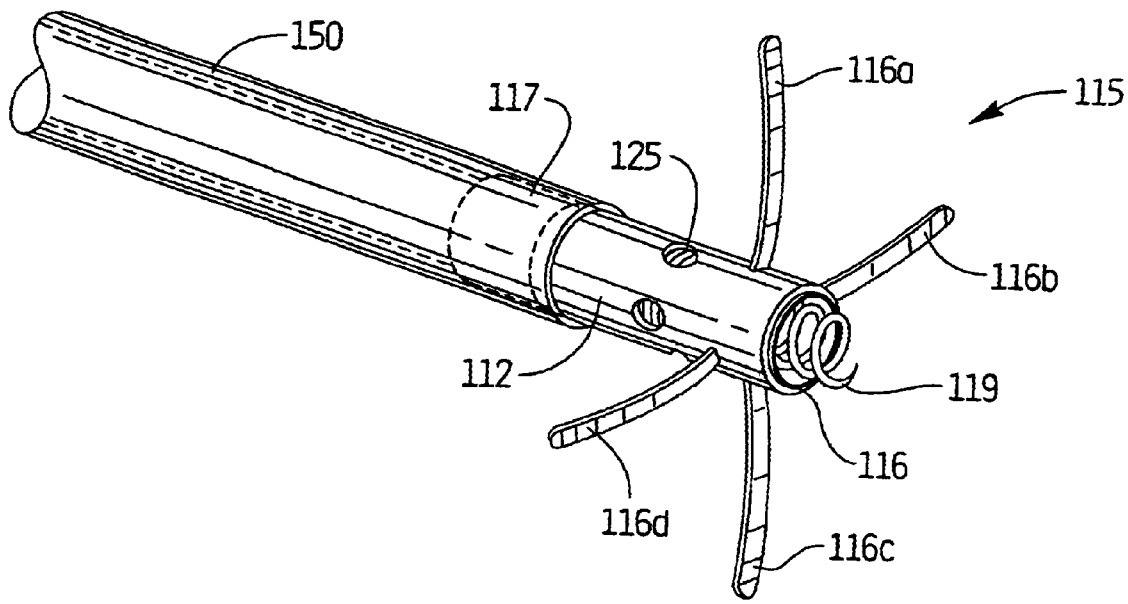
FIG_4
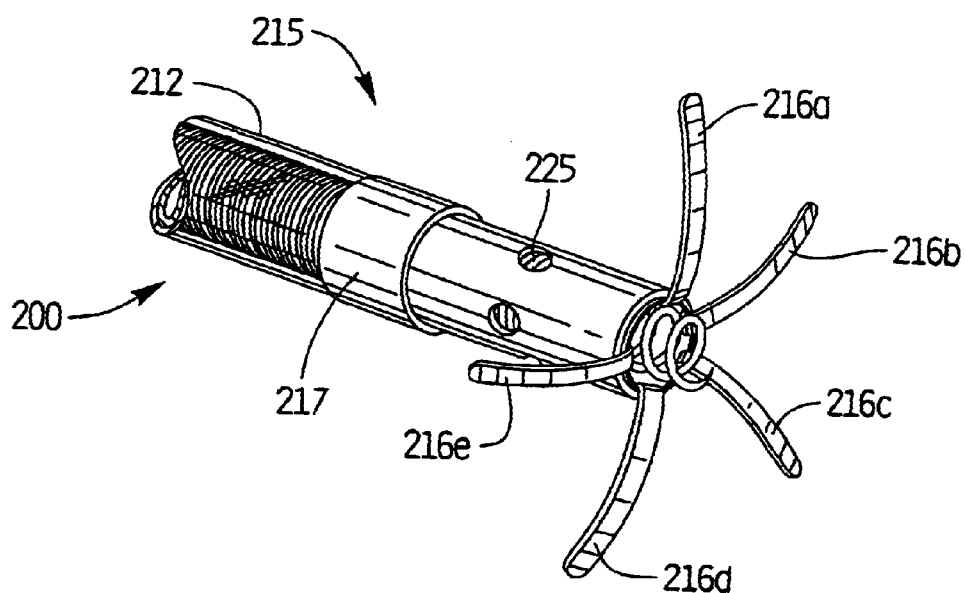
FIG_5

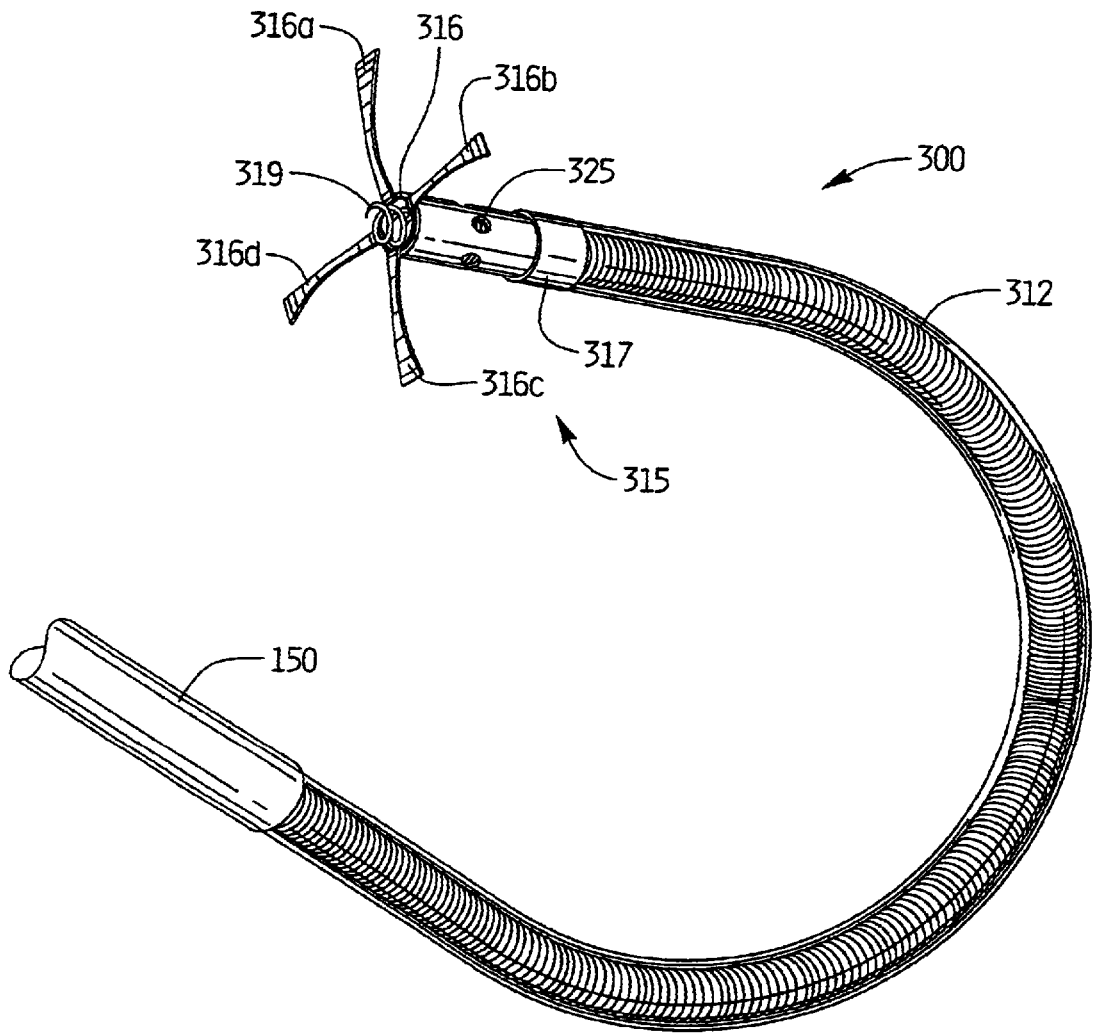
FIG_6

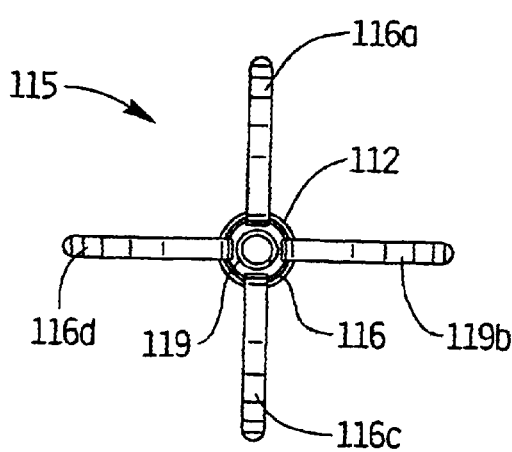
FIG_8
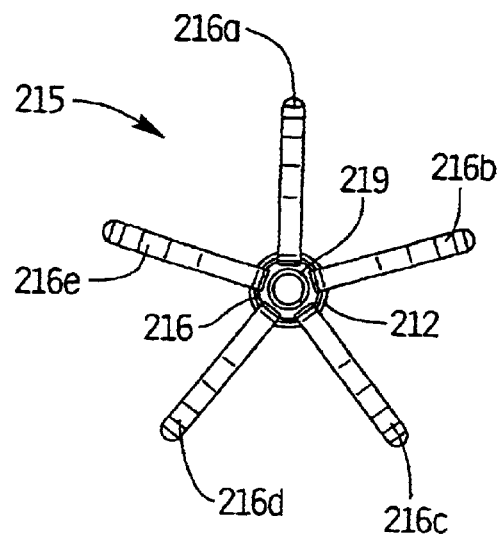
FIG_9
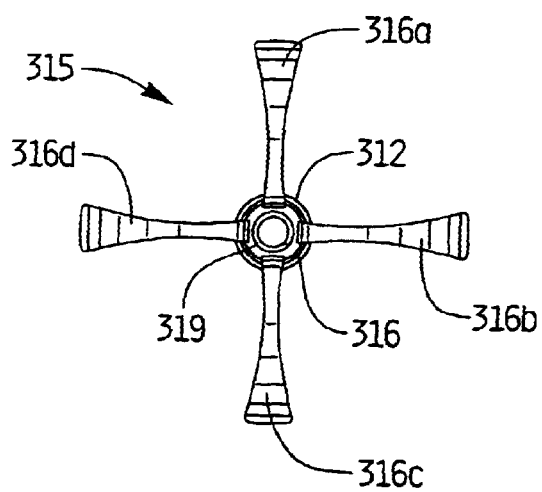
FIG_10
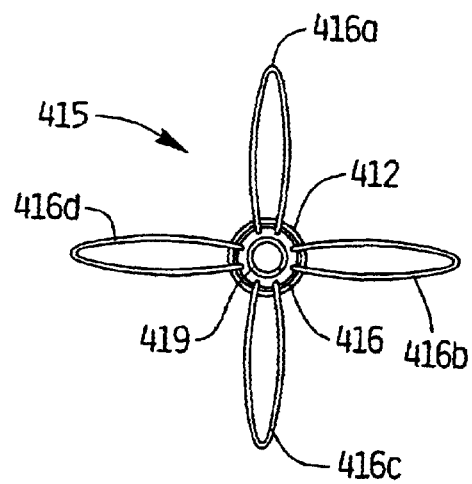
FIG_11

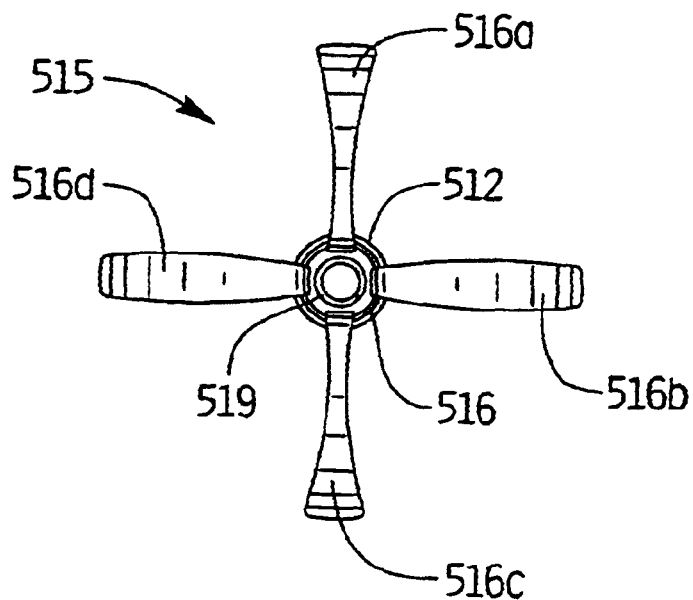
FIG_12a
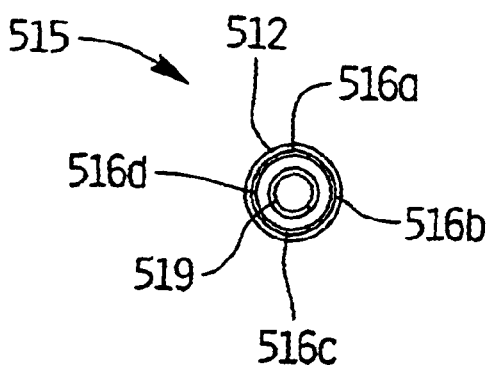
FIG_12b

ENDOCARDIAL LEAD

BACKGROUND OF THE INVENTION

1. Field of the Invention

The subject invention relates to an endocardial lead, and more particularly, to an implantable cardioversion and defibrillation lead for applying electrical energy to the heart.

2. Background of the Related Art

It is well known in the field of cardiology that certain types of cardiac arrhythmia known as ventricular tachycardia and fibrillation can be effectively treated by the application of electrical energy to the heart to defibrillate the fibrillating tissue. Implantable defibrillation leads have been developed to stimulate the heart when an arrhythmia occurs. These devices typically include electrodes that are placed adjacent to the inside wall of the heart. Electric current is applied to the electrode through an interconnected insulated electrode wire to stimulate the heart muscle which is in contact with the electrode.

In general, there are two types of endocardial lead tips. The first type is commonly referred to as a passive fixation tip and the second is known as an active fixation tip. An active fixation tip is of the screw-in type wherein a physician manually screws or engages a conductive electrode element into the heart wall. An example of a lead with a screw type fixating means is disclosed in U.S. Pat. No. 5,261,417 to Osypka. The passive fixation tip generally requires no action of the physician beyond insertion of the lead in a normal manner together with placement of the electrode tip in the apex of the ventricle. In order to stabilize the position of such a lead at the heart wall, tines made of thin wire or elastomeric material are used to entrap or hold the distal end of the lead in the trabeculae of the heart. An example of a lead with passive fixation means is disclosed in U.S. Pat. No. 4,945,922 to van Krieken.

It is preferable to have defibrillation leads that are easily implantable and which have substantially large surface areas to provide even current distribution and low energy thresholds. Thus, defibrillation leads are known which are collapsed into an advancement position for implantation in the body and subsequently deployed into an operating condition. Examples of such leads are disclosed in U.S. Pat. No. 5,282,845 to Bush et al. which defines a lead having a plurality of curvilinear electrodes, and U.S. Pat. No. 5,411,527 to Alt which defines a lead having a plurality of individual fiber strands. Neither prior art reference includes fixation means for stabilizing the position of the lead at the wall of the heart.

It would be beneficial to provide a defibrillation lead that is easily implantable, has a substantially large defibrillating surface area to provide even current distribution and low energy thresholds, and is configured for permanent active fixation at the wall of the heart.

SUMMARY OF THE INVENTION

The subject invention is directed to an implantable endocardial cardioversion and defibrillation lead for applying electrical energy to the heart which includes an elongated insulative lead body having opposed proximal and distal end portions, and having a lumen extending therethrough. An electrode assembly is operatively associated with the distal end portion of the lead body. The electrode assembly has a defibrillating surface for stimulating cardiac tissue and includes a distal tip electrode having a central annular portion and circumferentially disposed structural means extending radially from the central portion to define the area defibrillating surface.

A connector assembly is operatively associated with the proximal end portion of the lead body for facilitating electrical connection to an implanted automated defibrillator or a similar energy producing device. A coiled multifilar conductor assembly extends through the lumen of the lead body to electrically join the electrode assembly and the connector assembly.

In accordance with a preferred embodiment of the subject invention, the structural means extending radially from the central annular portion of the distal electrode tip is defined by a plurality of circumferentially spaced apart radially extendable arms. The arms are adapted and configured for movement between a first position wherein they are in an axially extended orientation (i.e., constrained within the tubular sheath of an introducer) and a second position wherein they are in a radially extended orientation. It is envisioned that the radially extendable arms can vary in configuration and number, and that they may be rearwardly or forwardly (proximally or distally) swept during percutaneous introduction.

The electrode assembly can include as few as three or as many as six or more circumferentially spaced apart radially extendable arms. Furthermore, the arms may be constructed from flat strips of material or from round wire stock. The electrode assembly is preferably formed from a biocompatible metal selected from the group consisting of platinum, iridium, platinum-iridium alloy, tantalum, and titanium. Alternatively, the arms may be formed from a shape memory alloy, such as, for example, a titanium-nickel alloy which will aide in the movement of the arms from a constrained position to a deployed position.

The elongated insulative lead body can have a generally linear configuration, or a preformed J-shaped configuration depending upon intended use, i.e., right ventricular or a trial implantation. The insulative lead body is preferably formed from a non-conductive material selected from the group consisting of polyurethane and silicone. It is envisioned that the lead may be configured for defibrillation, sensing or pacing in either a unipolar, bipolar or tripolar mode.

In a preferred embodiment of the subject invention, the lead includes a retractable fixation screw operatively associated with the distal end portion of the lead body for securing the lead assembly to cardiac tissue. Alternatively, the fixation screw may be stationary relative to the lead body. Preferably, the fixation screw is electrically active and forms part of the distal electrode assembly. However, it is envisioned that the fixation screw may be electrically insulated from the electrode assembly so as not to contribute in whole or in part to the electrode surface of the lead. In this instance, the screw would serve as a sensing pathway for the lead.

The subject invention is also directed to a method of implanting an endocardial lead which includes the step of introducing an endocardial defibrillation lead having an elongated lead body with an electrode assembly operatively associated with a distal end portion thereof, the electrode assembly and include a plurality of radially extendable arms configured for movement between an axially extended orientation and a radially extended orientation. The method further includes the step of moving the radially extendable arms from the axially extended orientation to the radially extended orientation. The method also includes the steps of providing a tubular introducer sheath for percutaneously introducing the lead and actively securing the distal end of the lead to cardiac tissue.

These and other unique features of the endocardial defibrillation lead of the subject invention and the method of constructing and using the same will become more readily apparent from the following description of the drawings taken in conjunction with the detailed of the preferred embodiments.

BRIEF DESCRIPTION OF THE DRAWINGS

So that those having ordinary skill in the art to which the subject invention appertains will more readily understand how to construct and use the endocardial defibrillation lead of the subject invention, reference may be had to the drawings wherein:

FIG. 2 is a perspective view of a distal end portion of an endocardial defibrillation lead constructed in accordance with a preferred embodiment of the subject invention which has a straight catheter body and a distal tip electrode with four radially extending arms and active fixation means, wherein the radially depending arms are disposed in a constrained position within a tubular introducer prior to the deployment thereof;

FIG. 3 is a perspective view of the distal end portion of the endocardial defibrillation lead of FIG. 2 with the four radially extending arms disposed in a outwardly radiating deployed position extended out from the distal end of the tubular introducer sheath;

FIG. 4 is a perspective view of the distal end portion of an alternative embodiment of the endocardial defibrillation lead of FIGS. 2 and 3 with the four radially extending arms spaced proximally from the distal tip of the lead body;

FIG. 5 is a perspective view of the distal end portion of an endocardial defibrillation lead constructed in accordance with a preferred embodiment of the subject invention which has a straight catheter body and a distal tip electrode with five radially extending arms and active fixation means;

FIG. 6 is a perspective view of the distal end portion of an endocardial defibrillation lead constructed in accordance with a preferred embodiment of the subject invention which has a J-shaped catheter body and a distal tip electrode with four outwardly flared radially extending arms and active fixation means;

FIG. 8 is a plan view of the distal portion of the endocardial lead illustrated in FIG. 3;

FIG. 9 is a plan view of the distal portion of the endocardial lead illustrated in FIG. 5;

FIG. 10 is a plan view of the distal portion of the endocardial lead illustrated in FIG. 6;

FIG. 11 is a plan view of the distal portion of the endocardial lead illustrated in FIG. 7; and FIGS. 12a and 12b are plan views of the distal portion of another endocardial constructed in accordance with a preferred embodiment of the subject invention, where FIG. 12a illustrates the arms of the electrode assembly in a radially extended position and FIG. 12b illustrates the arms of the electrode assembly in an axially extended position.

These and other features of the endocardial defibrillation lead of the subject invention and the method of using the same will become more readily apparent to those having ordinary skill in the art form the following detailed description of the preferred embodiments.

DETAILED DESCRIPTION OF THE PREFERRED EMBODIMENTS

Figure 1:
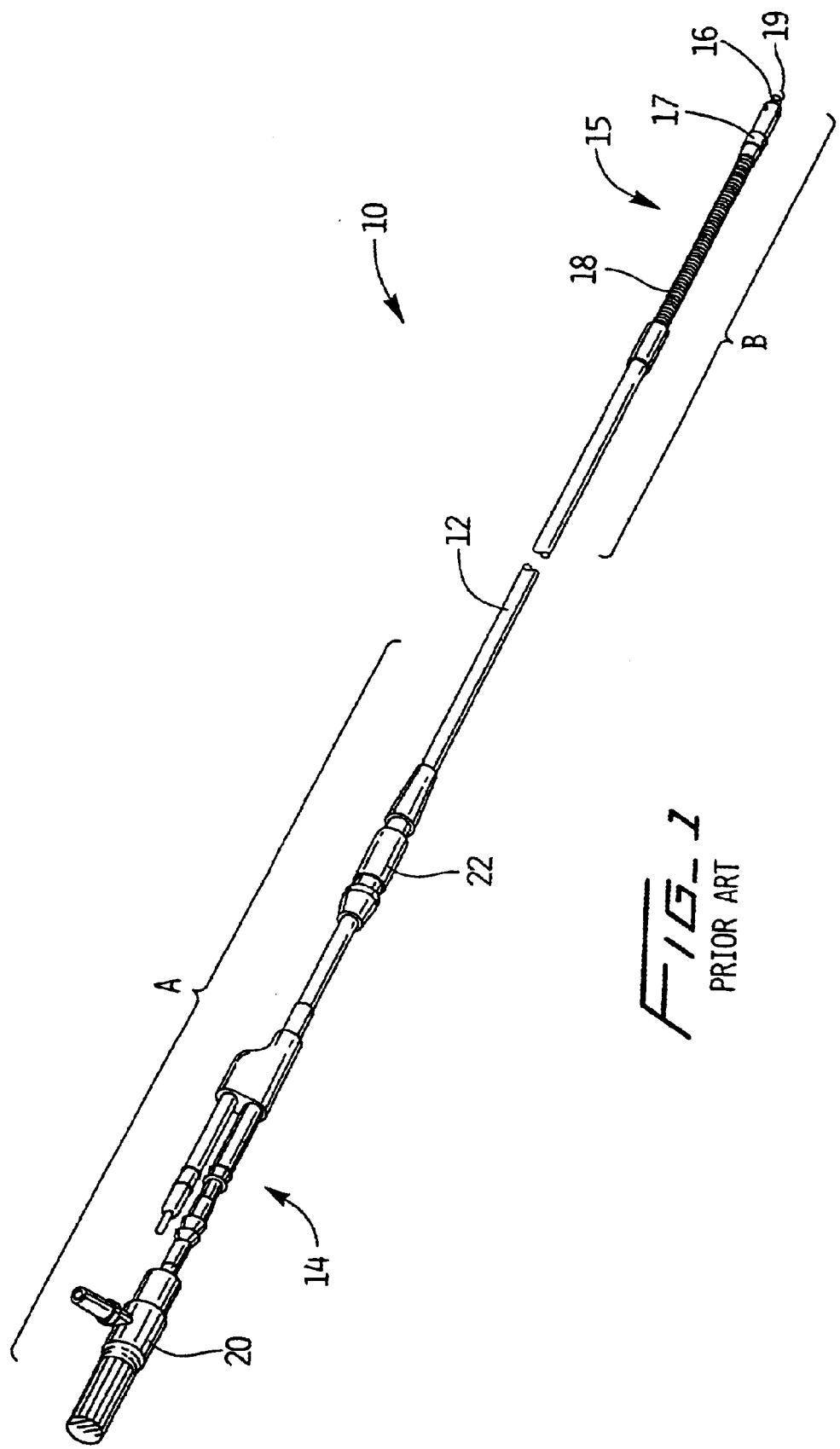
FIG. 1 is a perspective view of a prior art endocardial defibrillation lead which has a straight catheter body and a conventional distal tip electrode with active fixation means in the form of a retractable or stationary screw.

Referring now in detail to the drawings, there is illustrated in FIG. 1 a prior art tripolar endocardial defibrillation lead designated generally by reference numeral 10. Endocardial lead 10 is adapted for stimulation of the ventricle or atrial wall of the heart to effectuate cardioversion and/or defibrillation. As shown in FIG. 1, the lead 10 defines a proximal portion "A" and a distal portion "B" and includes an elongated insulated lead body 12. Lead body 12 is constructed of either polyurethane insulation or silicone rubber and defines an interior lumen.

A connector assembly 14.is provided at the proximal end of lead body 12 to facilitate electrical connection with an automated defibrillator or similar energy generating device (not shown). The lead has an electrode assembly 15 that includes a tip electrode 16 provided at the distal end of the lead body 12, a ring electrode 17 spaced proximally from the tip electrode and a helically coiled shock electrode 18. The tip electrode 16 typically has a diameter of about 8 mm and defines an electrode surface area of between 6 $mm^2$ and 10 $mm^2$. A section of lead body 12 separates and insulates the distal tip electrode 16 from the ring electrode 17. The ring electrode 17 is generally spaced about 5 to 15 mm from the tip electrode 16 and defines a surface area of about 30 to 40 $mm^2$. The helical shock electrode 18 generally has a length of about 4 cm, a diameter of about 4 mm, a surface area of about 3 $cm^2$ and is typically spaced about 15 to 20 mm from the tip electrode 16.

A coiled multifilar conductor wire, while not shown in FIG. 1, extends through the interior lumen of lead body 12 and electrically connects the proximal connector assembly 14 with the electrically active components of the electrode assembly 15. The electrically active components of the electrode assembly, are preferably formed from or coated with a bio-compatible metallic material, such as, platinum, iridium, platinum-iridium alloy, tantalum, titanium or a like material.

A retractable fixation screw 19 is operatively associated with the distal tip electrode 16 and is configured to facilitate active fixation of the lead to the wall of the heart. The helix of the fixation screw 19 is typically about 1.5 mm in length and may be electrically active so as to form part of the electrode surface area. In such an instance, the fixation screw may be used for fibrillation. Alternatively, the fixation screw may be electrically insulated from tip electrode 16, so as not to contribute, in whole or in part, to the surface of the electrode tip. In this instance, the screw would serve as a sensing pathway for the lead. Those skilled in the art will readily appreciate that alternative fixation means may be associated with the lead body, such as, for example, a set of flexible tines may be provided at the distal end of the lead body for passive fixation.

A screw driver stylet 20 is operatively associated with the proximal end of the lead body 12. It cooperates with a helix mechanism (not shown) at the distal end of the lead body to effectuate advancement and retraction of fixation screw 19. The fixation screw may also be stationary. In addition, a ligature sleeve 22 is provided on the lead body 12, and is movable along the length thereof, to support sutures which facilitate permanent placement of the lead body.

Referring now to FIGS. 2 and 3, there is illustrated, in the constrained and deployed conditions, respectively, the distal end portion of an endocardial defibrillation lead constructed in accordance with a preferred embodiment of the subject invention and designated generally by reference numeral 100. Endocardial lead 100 is substantially similar to the prior art lead of FIG. 1 in that the proximal portion of lead 100 is substantially identical to the proximal portion of lead 10. Lead 100 differs in that its electrode assembly 115 does not include an elongated coiled shock helix for defibrillation. Instead, the defibrillating surface of electrode assembly 115 includes a plurality of radially extending circumferentially spaced apart electrically active arms designated by reference numerals 116a–116d. These arms depend from the central annular electrode tip 116 of electrode assembly 115. The effective surface area of the defibrillating surface of electrode assembly 115 is thus significantly increased relative to that of the prior defibrillation device 10.

Electrode assembly 115 further includes a ring electrode 117 spaced proximally from the tip electrode 116 and the electrode arms 116a–116d. The ring electrode 117 enables the lead to operate in a bipolar mode. It is envisioned that the electrode assembly of the subject invention could be configured to operate in a unipolar mode. In such an instance, a ring electrode would not be provided as a second pole for the lead. Instead, to defibrillate the heart, a second pole may be provided by another unipolar lead placed in another chamber of the heart.

Lead 100 also includes an active fixation screw 119 for positively securing the electrode assembly 115 to the interior wall of the heart. The fixation screw 119 is adapted and configured for movement between a retracted position and an axially extended position through manipulation of a drive mechanism 20 associated with the proximal end portion of the lead body. During vascular introduction of the lead body, the fixation screw is disposed in the retracted position. Once the lead has been positioned within the heart, the fixation screw is extended in such a manner so as to engage cardiac tissue and thereby secure the distal end of the lead body to the interior wall of the heart.

As in the prior art device described hereinabove, fixation screw 119 is electrically active and forms part of the active surface area of electrode assembly 115. In certain instances, it may define a sensing pathway for the lead, and in other instances it may form part of the shocking surface of the lead. Alternatively, the fixation screw 119 may be electrically insulated from the distal tip electrode 116 and would not form part of the electrically active surface area of the lead. The electrically active components of electrode assembly 115 receive electrical energy from the connector assembly 14 associated with the proximal end portion of the lead body through a multifilar conductor wire 125 that extends through the interior lumen of the insulated linear lead body 112. The multifilar conductor is preferably a low impedance coiled quadrifilar (four wire) conductor or a similar low impedance conductor having a silver core with a stainless steel outer wrap.

In use, the distal end portion of endocardial lead 100 is percutaneously introduced into a blood vessel through a tubular introducer sheath 150. Initially, when the distal portion of the lead is disposed within the tubular sheath 150, the electrode arms 116a–116d are swept forward (distally) in a constrained (stressed) position, as shown in FIG. 2. It is also envisioned that the arms may be rearwardly (proximally) swept during introduction. In either case, upon introduction of the lead into a blood vessel, i.e., when the electrode arms 116a–116d are extended out from the distal end of the tubular sheath 150, the arms deploy into a radially extended (unstressed) position, as shown in FIGS. 3. In such a position, the central tip portion 116 and the radially extended arms 116a–116d define the defibrillation or shock surface of the endocardial lead 100.

The effective surface area of the defibrillation portion of electrode assembly 115 is significantly greater than the effective surface area of the coiled shock helix 17 that defines the defibrillation surface of the prior art lead 10 shown in FIG. 1. Moreover, those skilled in the art will readily appreciate that the effective surface area of the prior art shock helix 17 is limited by the diameter and length of the helical coil, which is typically 7F to 10F in diameter and 4 to 5 cm in length. More particularly, the diameter of the shock helix must be compliant with the size of the vascular introducer utilized to deploy the lead, and the length of the shock helix must comply with the anatomy of the patient within which the device is deployed. In contrast, regardless of how long or broad the electrode arms 116a–116d are, they do not add to the overall diameter of the lead body when they are swept forward during introduction, as best seen in FIG. 2. Furthermore, in the deployed position, the arms of electrode assembly 115 do not extend over as long a distance as the elongated shock helix 17. Thus the defibrillation electrode of the subject invention is more anatomically compliant than the prior art shock electrode.

As shown in FIG. 4, in an alternative embodiment of the subject invention the radially extending electrode arms 116a–116d are axially spaced from the central tip electrode 116 and project radially outwardly from lead body 112 through a set of apertures formed therein. In such an instance, the electrode tip 116 is electrically insulated from the defibrillating surface defined .by the electrode arms 116a–116d and may serve as a sensing pathway or as a pacing surface for the lead. With the arms spaced from the distal electrode tip, the lead can operate in a tripolar mode with the proximal ring electrode 117 and the distal tip electrode 116 acting as anode and cathode, respectively. Thus, the lead may be used for multiple functions includes defibrillating, sensing and pacing.

Referring now to FIG. 5, there is illustrated another embodiment of an endocardial defibrillation lead constructed in accordance with a preferred embodiment of the subject invention and designated generally by reference numeral 200. Lead 200 is substantially similar in structure and function to endocardial lead 100 in that it includes a proximal ring electrode 217 providing bipolarity for the device, a fixation screw 219 for securing the distal end of the lead body 212 to cardiac tissue that may or may not be electrically active, and a multifilar conductor wire for delivering energy to the electrode assembly 215 from a proximal connector assembly 14. Lead 200 differs however, in that defibrillating portion of electrode assembly 215 includes five radially extending electrode arms 216a–216e which depend from the central tip portion 216 (see FIG. 9) rather than the four radial arms of electrode 115. The additional electrode arm further enhances the area of the defibrillating surface of electrode assembly 215 so as to maximize the energy delivered to the heart tissue by lead 200 during defibrillation.

Referring now to FIG. 6, there is illustrated another embodiment of an endocardial lead constructed in accordance with a preferred embodiment of the subject invention and designated generally by reference numeral 300. Lead 300 is substantially similar in structure and function to endocardial lead 200 in that it includes a proximal ring electrode 317, a fixation screw 319, and a multifilar conductor wire 325 extending through the lumen of the lead body 312, which is generally J-shaped in configuration, for delivering energy to the electrode assembly 315 from a proximal connector assembly 14. It differs however, in that the electrode assembly 315 of lead 300 includes a central tip portion 316 and four radially extending electrode arms 316a–316d that have flared radially outer portions (see FIG. 10), rather than generally uniform profiles as the arms of electrode assemblies 115 and 215. The additional flared surface area of each electrode arm of electrode assembly 315 further enhances the surface area of the defibrillating surface of electrode assembly 315 to maximize the energy delivered to the heart tissue during defibrillation.

Figure 7:
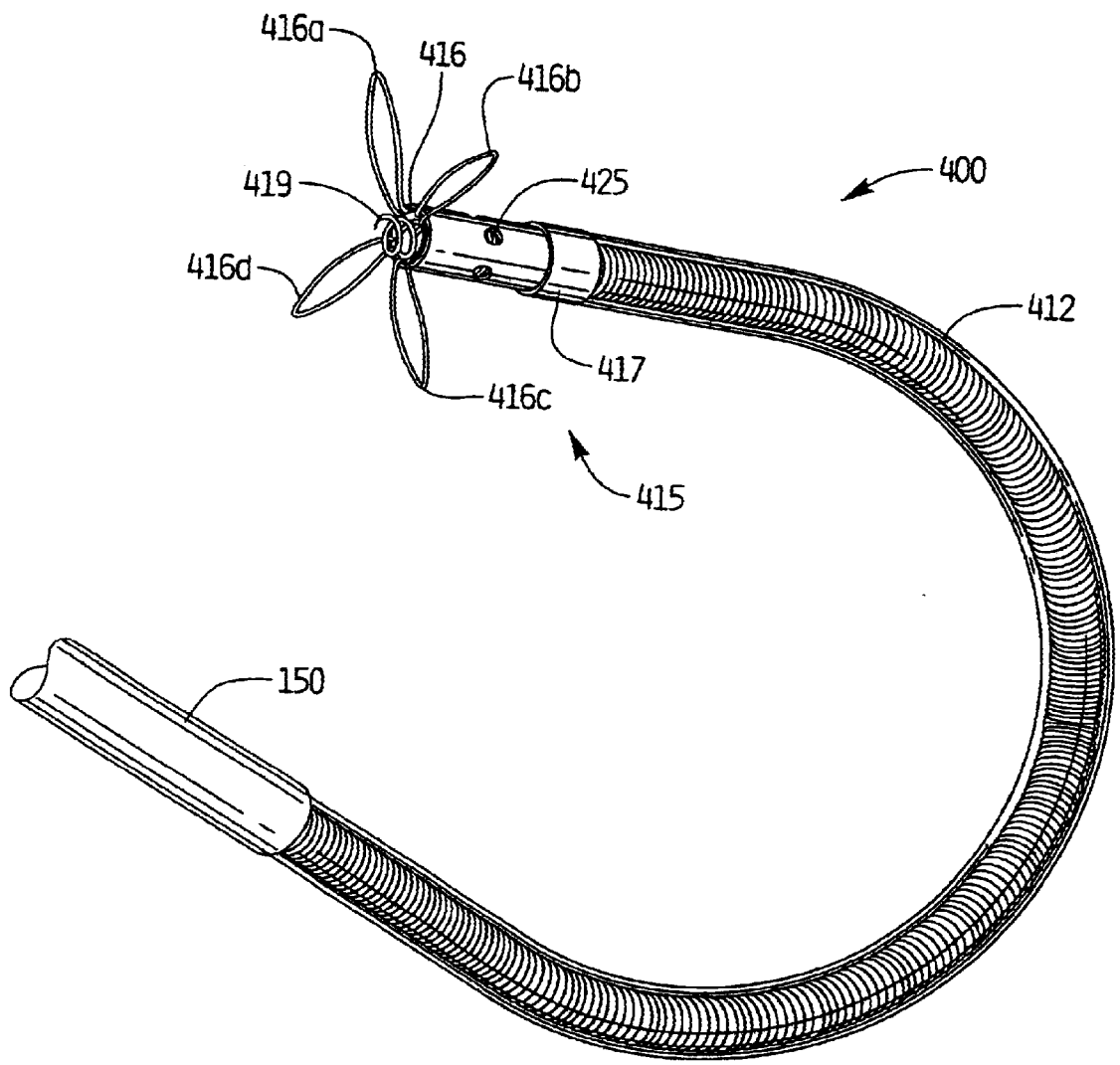
FIG. 7 is a perspective view of the distal end portion of an endocardial defibrillation lead constructed in accordance with a preferred embodiment of the subject invention which has a J-shaped catheter body and a distal tip electrode with four radially extending looped arms and active fixation means.

Another embodiment of an endocardial lead constructed in accordance with a preferred embodiment of the subject invention is illustrated in FIG. 7, and designated generally by reference numeral 400. Lead 400 is also substantially similar in structure and function to lead 300 in that it includes a ring electrode 417, a fixation screw 419, and a multifilar conductor wire 425 that extends through the interior lumen of J-shaped lead body 412. Lead 400 differs from lead 300 in that the electrode assembly 415 of lead 400 includes four electrode loops 416a–416d that extend radially outwardly from the central tip portion 416 of the electrode assembly (see FIG. 11). The electrode loops, like the arms of the previous embodiments of the subject invention, define additional surface area to enhance the defibrillating surface of the electrode and thereby maximize the energy delivered to the heart tissue during stimulation.

Referring to FIGS. 12a and 12b, there is illustrated another lead assembly constructed in a accordance with a preferred embodiment of the subject invention and designated generally by reference numeral 515. Electrode assembly 515 includes four electrode arms 516a–516d that are configured to interfit with one another when the electrode assembly is disposed in an axially extended position, as best seen in FIG. 12a. Electrode arms 516a and 516c have concave lateral edges configured to mate with the convex lateral edges of electrode arms 516b and 516d when the four arms are swept forward. The four arms have a curved or arcuate profile which form a cylindrical shape when interfit with one another, as shown in FIG. 12b.

Preferably, the electrode arms and the central annular portion of the distal electrode of each embodiment of the subject invention are formed from the same or similar bio-compatible metallic material. For example, the central portion and arms of the electrode may be formed from platinum, iridium, platinum-iridium alloy, tantalum or titanium or a similar bio-compatible material. Alternatively, to better aide in the active deployment of the electrode arms from a constrained position to an unstressed deployed position, the arms may be constructed from a shape memory alloy, such as, for example, an alloy of nickel and titanium, or a spring metal with similar elastic properties. As illustrated in FIGS. 5–7, the electrode arms of each endocardial lead have a slight arcuate bow or curvature to enhance the surface contact of the electrode with the wall of the heart once the distal tip has been secured in place with the fixation screw. As illustrated, the overall configuration of the arms can vary within the scope of the subject disclosure. For example, the arms can be formed from flat metal or wire stock as shown, or from wound single or multifilar coils or helixes.

Furthermore, it is envisioned that the electrode arms may be integrally or monolithically formed with the central tip portion of the electrode or the structures may be joined to one another by conventional means known in the art, such as welding or the like. Alternatively, it is envisioned that the arms may be mechanically connected to the central portion of the electrode by conventional means such as hinges or the like.

It should be readily understood by those skilled in the art that each of the distal electrode assemblies disclosed herein are interchangeable. In other words, any one of the disclosed electrode assemblies could be utilized with a straight lead body or a J-shaped lead body. Thus, the embodiments of the invention described and illustrated in the subject application should only be viewed as exemplary embodiments of the subject invention.

Although the disclosed apparatus has been described with respect to preferred embodiments, it is apparent that modifications and changes can be made thereto without departing from the spirit and scope of the invention as defined by the appended claims.

What is claim is:

1. A bipolar endocardial defibrillation lead comprising:
   a) an elongated insulative lead body having opposed proximal and distal end portions, and having an interior lumen extending therethrough;
   b) a shock electrode having an electrically active central annular portion disposed at the distal end of the lead body and a plurality of electrically active defibrillation arms depending from electrically connected to the central annular portion for delivering electrical energy to cardiac tissue, wherein the arms are configured for movement from an axially extended position located outside the interior lumen of the lead body to a radially extended position relative to the central annular portion of the shock electrode;
   c) a ring electrode operatively associated with the lead body and spaced proximally from the shock electrode;
   d) a fixation screw disposed axially within the central annular portion of the shock electrode for securing the distal end portion of the lead body to cardiac tissue;
   e) a connector assembly operatively associated with the proximal end portion of the lead body to facilitate electrical connection with an automated energy generating device; and
   f) a coiled multifilar conductor assembly extending through the lead body to electrically join the shock electrode and the ring electrode to the connector assembly.

2. A bipolar endocardial defibrillation lead as recited in claim 1, wherein the fixation screw is electrically active.

3. A bipolar endocardial defibrillation lead as recited in claim 1, wherein the fixation screw is electrically insulated from the central annular portion of the shock electrode.

4. A bipolar endocardial defibrillation lead as recited in claim 1, wherein the fixation screw is mounted for axial movement between a retracted position and an extended position.

5. A bipolar endocardial defibrillation lead as recited in claim 1, wherein the lead body has a preformed J-shaped configuration.

6. A bipolar endocardial defibrillation lead as recited in claim 1, wherein the lead body has a generally linear configuration.

7. A bipolar endocardial defibrillation lead as recited in claim 1, wherein the arms are formed from strips of conductive material.

8. A bipolar endocardial defibrillation lead as recited in claim 1, wherein the arms are formed from loops of conductive material.

9. A bipolar endocardial defibrillation lead as recited in claim 1, further comprising a tubular introducer sheath for maintaining the defibrillation arms in the axially extended position during introduction of the lead.

10. A bipolar endocardial defibrillation lead comprising:
  a) an elongated insulative lead body having opposed proximal and distal end portions, and having an interior lumen extending therethrough;
  b) a shock electrode having an electrically active central annular portion disposed at the distal end of the lead body and a plurality of electrically active defibrillation arms depending from electrically connected to the central annular portion for delivering electrical energy to cardiac tissue, wherein the arms are configured for movement from an axially extended position located outside the interior lumen of the lead body to a radially extended position relative to the central annular portion of the shock electrode;
  c) a ring electrode operatively associated with the lead body and spaced proximally from the shock electrode;
  d) a connector assembly operatively associated with the proximal end portion of the lead body to facilitate electrical connection with an automated energy generating device;
  e) a coiled multifilar conductor assembly extending through the interior lumen of the lead body to electrically join the shock electrode and the ring electrode to the connector assembly; and
  f) a tubular introducer sheath for maintaining the defibrillation arms in an axially extended position during introduction of the lead.

11. A bipolar endocardial defibrillation lead as recited in claim 10, further comprising a fixation screw disposed axially within the central annular portion of the shock electrode for securing the distal end portion of the lead body to cardiac tissue.

12. A bipolar endocardial defibrillation lead as recited in claim 11, wherein the fixation screw is electrically active.

13. A bipolar endocardial defibrillation lead as recited in claim 11, wherein the fixation screw is electrically insulated from the central annular portion of the shock electrode.

14. A bipolar endocardial defibrillation lead as recited in claim 11, wherein the fixation screw is mounted for axial movement between a retracted position and an extended position.

15. A bipolar endocardial defibrillation lead as recited in claim 10, wherein the lead body has a preformed J-shaped configuration.

16. A bipolar endocardial defibrillation lead as recited in claim 10, wherein the lead body has a generally linear configuration.

17. A bipolar endocardial defibrillation lead as recited in claim 10, wherein the arms are formed from strips of conductive material.

18. A bipolar endocardial defibrillation lead as recited in claim 10, wherein the arms are formed from loops of conductive material.

* * * * *